United States Patent
Kuhn et al.

(10) Patent No.: US 10,144,878 B1
(45) Date of Patent: Dec. 4, 2018

(54) SYSTEMS AND METHODS FOR PRODUCING LIQUID FUELS FROM LANDFILL GASES

(71) Applicants: John N. Kuhn, Tampa, FL (US); Babu Joseph, Tampa, FL (US); Devin Walker, Lutz, FL (US); Syed Ali Gardezi, Tampa, FL (US); Timothy Roberge, Tampa, FL (US)

(72) Inventors: John N. Kuhn, Tampa, FL (US); Babu Joseph, Tampa, FL (US); Devin Walker, Lutz, FL (US); Syed Ali Gardezi, Tampa, FL (US); Timothy Roberge, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/985,822

(22) Filed: May 22, 2018

Related U.S. Application Data

(62) Division of application No. 14/029,079, filed on Sep. 17, 2013, now Pat. No. 10,005,963.

(60) Provisional application No. 61/703,428, filed on Sep. 20, 2012.

(51) Int. Cl.
 *C10G 2/00* (2006.01)
 *B01J 23/00* (2006.01)
 *B01J 23/78* (2006.01)
 *C07C 1/12* (2006.01)

(52) U.S. Cl.
 CPC .......... *C10G 2/341* (2013.01); *B01J 23/002* (2013.01); *B01J 23/78* (2013.01); *C07C 1/12* (2013.01); *B01J 2523/00* (2013.01); *B01J 2523/3712* (2013.01); *B01J 2523/48* (2013.01)

(58) Field of Classification Search
 CPC .......... C10G 2/341; C10G 2/331; B01J 23/78; B01J 23/002; B01J 2523/00; B01J 2523/48; B01J 2523/3712
 See application file for complete search history.

(56) References Cited

U.S. PATENT DOCUMENTS

| | | |
|---|---|---|
| 4,678,860 A | 7/1987 | Kuester |
| 4,728,672 A | 3/1988 | Yoshinari et al. |
| 5,186,722 A | 2/1993 | Cantrell et al. |
| 5,727,903 A | 3/1998 | Borray et al. |
| 5,830,423 A | 11/1998 | Trocciola et al. |

(Continued)

OTHER PUBLICATIONS

Douglas C. Elliott, et al., "Liquid hydrocarbon fuels from biomass", Amer. Chem Soc., Div. Fuel Chem., 34(4):1160-1166, 1989.

(Continued)

*Primary Examiner* — Lessanework Seifu
(74) *Attorney, Agent, or Firm* — Thomas | Horstemeyer, LLP

(57) ABSTRACT

In some embodiments, method for producing liquid fuel from landfill gas, the method including providing landfill gas to a tri-reformer, performing a tri-reforming process on the landfill gas within the tri-reformer to convert the landfill gas into synthesis gas, wherein the tri-reforming process combines carbon dioxide reforming, steam reforming, water-gas shifting, and methane oxidation and wherein the synthesis gas has a $H_2:CO$ ratio of approximately 2:1, providing the synthesis gas to a Fischer-Tropsch synthesis (FTS) reformer, and converting the synthesis gas into liquid fuel within the FTS reformer.

15 Claims, 7 Drawing Sheets

(56) References Cited

U.S. PATENT DOCUMENTS

| | | |
|---|---|---|
| 5,902,915 A | 5/1999 | Melnichuk et al. |
| 6,071,326 A | 6/2000 | Hall |
| 7,332,146 B1 | 2/2008 | Huang et al. |
| 7,753,973 B2 | 7/2010 | Galloway |
| 7,964,761 B2 | 6/2011 | Zmierczak et al. |
| 8,088,832 B2 | 1/2012 | Melnichuk et al. |
| 8,153,850 B2 | 4/2012 | Hall et al. |
| 8,187,568 B2 | 5/2012 | Guenther |
| 8,378,159 B2 | 2/2013 | Corradini et al. |
| 8,444,725 B2 | 5/2013 | Agrawal et al. |
| 8,518,680 B2 | 8/2013 | Kuhry et al. |
| 2008/0108716 A1 | 5/2008 | Ayasse |
| 2010/0175320 A1 | 7/2010 | Schuetzle et al. |
| 2011/0239543 A1 | 10/2011 | Park et al. |
| 2012/0095272 A1 | 4/2012 | El-Halwagi et al. |

OTHER PUBLICATIONS

Juan Carlos Serrano-Ruiz, et al., "Catalytic routes for the conversion of biomass into liquid hydrocarbon transportation fuels", Energy Environ. Sci., 4:83-99, 2011.

Ayhan Demirbas, "Biomass resource facilities and biomass conversion processing for fuels and chemicals", Energy Conversion and Management, 42:1357-1378, 2001.

Devin M. Walker, et al., "Synthesis gas production to desired hydrogen to carbon monoxide ratios by tri-reforming of methane using Ni—MgO—(Ce,Zr)O2 catalysts", Applies Catalysis A: General, 445-446:61-68, 2012.

Devin Walker, et al., "Catalytic tri-reforming of biomass-derived syngas to produce desired H2:CO ratios for fuel applications", Department of Chemical and Biochemical Engineering, University of South Florida.

"When waste is no longer waste", Alternative fuels corporation, Blue Water Sustainability Presentation, Nov. 2009.

SYSTEMS AND METHODS FOR PRODUCING LIQUID FUELS FROM LANDFILL GASES

CROSS-REFERENCE TO RELATED APPLICATION(S)

This application is a divisional application of co-pending U.S. Non-Provisional Application entitled "Systems And Methods For Producing Liquid Fuels From Landfill Gases," having Ser. No. 14/029,079 and filed Sep. 17, 2013, and claims priority to U.S. Provisional Application Ser. No. 61/703,428, filed Sep. 20, 2012, which is hereby incorporated by reference herein in its entirety.

BACKGROUND

There has been a recent shift towards using fuels produced from renewable resources in today's environmentally conscious world. Biomass found in municipal solid waste (MSW) provides an excellent opportunity as a major, near-term, carbon-neutral energy resource. MSW naturally biodegrades, producing landfill gas (LFG) composed mainly of methane and carbon dioxide, two major greenhouse gases, which can be used to generate the fuels.

Despite the potential benefits of processing MSW to generate liquid fuels, less than 15% of the over 243 million tons of MSW produced each year is used for that purpose. One reason for this is that landfills currently lack robust technologies that can efficiently convert environmentally harmful hydrocarbons produced in LFG into liquid fuels. Existing technologies are inhibited by high capital costs and low economic recovery and therefore require carbon capture credits to be economically feasible. Current technologies also require specific deliverables in order to function as designed. If feedstock flows are outside the required specifications, the LFG is flared and the resource is effectively wasted.

New LFG-to-liquids processes could provide high economic returns from an abundant and renewable feedstock. At the current prices of diesel and jet fuel, the end product would be an attractive alternative to power generation. Once a landfill is outfitted with an LFG-to-liquids plant, the fuel product could also be used to decrease fuel requirements needed to perform ordinary landfill tasks. Additionally, the fuel product could further be marketed to interested parties because it is compatible with existing infrastructure.

In view of the above discussion, it can be appreciated that it would be desirable to have alternative systems and methods for producing liquid fuels from MSW and/or LFG.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have alternative systems and methods for producing liquid fuels from municipal solid waste (MSW) and/or landfill gas (LFG). Disclosed herein are examples of systems and methods designed for this purpose. In some embodiments, the systems and methods use only two reactors to convert LFG into liquid fuel. In other embodiments, the systems further utilize solar energy to assist in the conversion.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
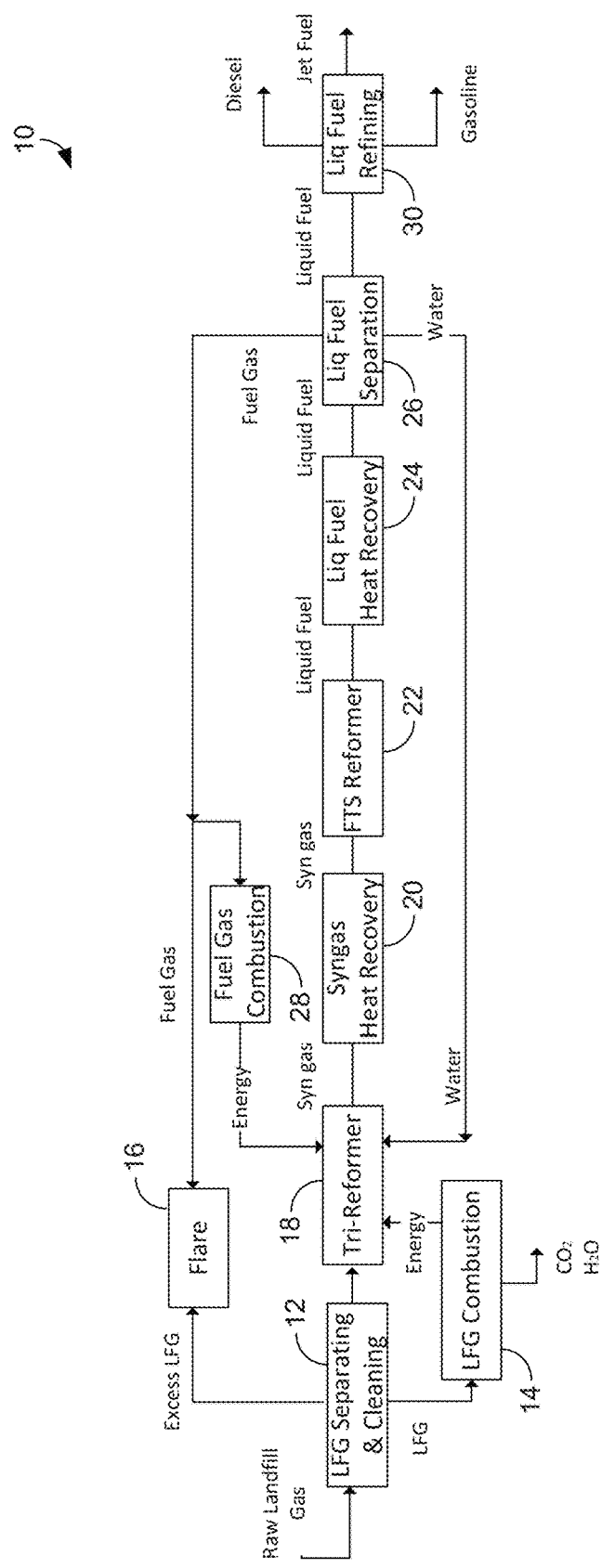
FIG. 1 is a block diagram of a first embodiment of a liquid fuel production system.

FIG. 1 illustrates a first embodiment of a fuel production system 10. As is shown in that figure, raw LFG is input into an LFG separating and cleaning unit 12 that separates particulate matter from the gas. The LFG is primarily composed of methane ($CH_4$) and carbon dioxide ($CO_2$). By way of example, the LFG can flow into the cleaning unit 12 at a rate of approximately 3,000 standard cubic feet per minute (scf/min). After being cleaned, the LFG leaves the cleaning unit 12 and passes into a tri-reformer 18 described below. In addition, some of the LFG can pass into an LFG combustion unit 14 in which the LFG is combusted by mixing it with oxygen ($O_2$) or air to provide heat for the reaction in the tri-reformer 18. By way of example, the LFG is heated within the LFG combustion unit 14 to a temperature of approximately 600° C. to 800° C. As is also shown in FIG. 1, $CO_2$ and water can be output from the LFG combustion unit 14 as by-products of the combustion process. In addition, excess LFG that is not needed for the production of liquid fuel can be delivered from the cleaning unit 12 to a flare unit 16 to be flared (i.e., combusted). The by-products of such flaring are $CO_2$ and water.

As noted above, LFG from the separating and cleaning unit 12 and the combustion unit 14 can be delivered to the tri-reformer 18 for processing. The tri-reforming process involves a combination of $CO_2$ reforming (Equation 1), steam reforming (Equation 2), water-gas shift (Equation 3), and methane oxidation (Equations 4 and 5) in a single reactor.

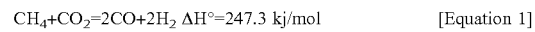

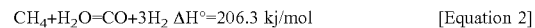

$$CO + H_2O = CO_2 + H_2 \quad \Delta H° = -41 \text{ kj/mol} \quad \text{[Equation 3]}$$

$$CH_4 + \tfrac{1}{2}O_2 = CO + 2H_2 \quad \Delta H° = -35.6 \text{ kj/mol} \quad \text{[Equation 4]}$$

$$CH_4 + 2O_2 = CO_2 + 2H_2O \quad \Delta H° = -880 \text{ kj/mol} \quad \text{[Equation 5]}$$

Use of the tri-reforming process eliminates the serious problem of carbon formation and high energy consumption commonly seen in $CO_2$ reforming by incorporating $H_2O$ and $O_2$ (see Equations 6, 7, 8, 9, and 10 below). Heat is generated in-situ that can be used to increase energy efficiency and achieve a thermo-neutral balance of reactions. $H_2$ and $CO$ selectivity can also be adjusted by controlling the amount of steam and $CO_2$ added to the reaction. This provides an important role in both industrial and environmental applications allowing production of high-value chemicals via oxo-synthesis, electricity via solid oxide fuel cells or molten carbonate fuel cells, and clean-burning hydrocarbon fuels via Fischer-Tropsch synthesis (FTS).

Coke Formation $$CH_4 = C + 2H_2 \quad \Delta H° = 74.9 \text{ kj/mol} \quad \text{[Equation 6]}$$

$$2CO = C + CO_2 \quad \Delta H° = 172.9 \text{ kj/mol} \quad \text{[Equation 7]}$$

Coke Destruction $$C \text{ (ads)} + CO_2 = 2CO \quad \Delta H° = 172.2 \text{ kj/mol} \quad \text{[Equation 8]}$$

$$C \text{ (ads)} + H_2O = CO + H_2 \quad \Delta H = ° \ 131.4 \text{ kj/mol} \quad \text{[Equation 9]}$$

$$C \text{ (ads)} + O_2 = CO_2 \quad \Delta H° = -393.7 \text{ kj/mol} \quad \text{[Equation 10]}$$

The tri-reforming catalyst used in the tri-reforming process must be thermally stable, have a high surface area, have high oxygen storage capacity (OSC), have good redox properties, provide resistance to coke formation, and be economically advantageous. Ni-based catalysts have shown good potential for reforming methane and provide a more economically friendly option over noble metals. However, Ni has the disadvantage of being susceptible to coke formation. Deactivation is directly related to the catalyst structure and composition and, therefore, research has been aimed at producing a suitable catalyst in the upgrading of MSW synthesis gas (or "syngas"). $CeO_2$ has a high oxygen storage capacity (OSC) and can be used as a promoter with Ni for methane conversion to syngas. The addition of $ZrO_2$ to $CeO_2$ has been shown to improve OSC, redox property, thermal stability, metal dispersion, selectivity, and catalytic activity. These improved characteristics are attributed to the formation of a $(Ce, Zr)O_2$ solid solution. Others have attributed the increased OSC from modifying the local oxygen environment around Ce and Zr and generating active oxygen. This result may be explained by the introduction of undersized Zr ions into the Ce framework that helps compensate for the volume increase associated with the valence change of $Ce^{4+}$ to $Ce^{3+}$, easing the transition. Research has shown that the Ce/Zr mixed oxides consistently perform with higher activity compared to the pure oxide supports and $Al_2O_3$ due to its ability to promote partial oxidation of methane (POM) and steam-reforming reactions. Because of this, $Ce_{1-x}Zr_xO_2$ support materials have received much attention with $0.6 < x < 0.8$ being preferred for catalytic applications.

Basic oxides, such as magnesia and zirconia, have been shown to catalyze the gasification of coke with steam and help prevent deposition of carbon in dry reforming. This phenomenon may be attributed to the low concentration of Lewis sites and increase of oxygen vacancies by introducing $ZrO_2$ and MgO into the catalyst composition. By coupling these basic oxides with Ni, catalysts promote $CO_2$ and $H_2O$ adsorption leading to enhanced $CO_2$ conversion and $H_2$ production. The enhanced $CO_2$ conversion has been attributed to a higher interface between Ni, MgO, and $ZrO_2$ resulting from NiO/MgO and $ZrO_2$/MgO solid solutions.

Experimentation was performed to determine which catalysts would be best for liquid fuel production. This experimentation and catalyst synthesis is described in the following paragraphs.

Ce/Zr oxide supports were prepared using the co-precipitation method reported by Rossignol et al. using $Ce(NO_3)_3 \times 6H_2O$ and $ZrO(NO_3)_2 \times H_2O$ as precursors. Pure ceria and zirconia oxides, as well as the mixed oxides with Ce:Zr molar ratios of 0.16:0.84, 0.6:0.4, and 0.8:0.2 were all prepared using the same method. Appropriate quantities of the precursor salts were dissolved in deionized (DI) water and precipitated by the addition of $NH_4OH$ to form hydrous zirconia, ceria, or Ce/Zr solution. This precipitate was vacuum-filtered and re-dispersed into a 0.25 M $NH_4OH$ solution. This dilute, basic solution was again vacuum-filtered and dried in an oven at 120° C. overnight. The dried powder was then calcined at 800° C. for 4 hours.

The loading of Ni and Mg to the oxide support was carried out using two different loading procedures: wet impregnation (WI) and deposition precipitation (DP). All metals were loaded on a mass basis to achieve desired weight percentage of metal on the catalyst. For the WI method, appropriate amounts of $Mg(NO_3)_2 \times H_2O$ and $Ni(NO_3)_2 \times 6H_2O$ were dissolved in deionized water to form a homogeneous solution. This solution was then added drop-wise to the support until incipient wetness and dried at 120° C. for 2 hours. This step was repeated until all of the metal nitrate solution had been added to the support. Following the final drying step, the catalyst was calcined at 500° C. for 4 hours. DP was performed using a modified method adapted from Li et al. Appropriate amounts of $Mg(NO_3)_2 \times H_2O$ and $Ni(NO_3)_2 \times 6H_2O$ where added to a volumetric flask and dissolved in 25 ml DI water. The powder support was added to the metal-salt solution and mixed with a stir plate to form a slurry. In a separate beaker, $CO(NH_2)_2$ (urea) was added in excess to 10 ml of DI water to achieve a 1:4 ratio of total metal nitrates: urea. The urea solution was added drop-wise to the metal-salt solution while stirring. The top of the volumetric flask was sealed to prevent evaporation of the solution and heated to 115° C. while stirring at 600 rpm on a heated stir plate. Urea hydrolyzes slowly at temperature allowing hydroxyl groups to react rapidly as they form, maintaining a constant pH and allowing precipitation on the surface and interior of pores. The solution was aged for 24 hours and then cooled to room temperature before vacuum-filtering with a Buchner funnel. Cold DI water was used to wash any remaining precursors and impurities from the filtered catalyst. The catalyst was then dried at 120° C. for 4 hours followed by calcination at 500° C. for 4 hours.

Braunauer-Emmett-Teller (BET), x-ray diffraction (XRD), temperature-programmed reduction (TPR), scanning electron microscopy-energy dispersive x-ray spectroscopy (SEM-EDS), and x-ray photoelectron spectroscopy (XPS) were used to characterize catalysts. The combination of these techniques provides valuable data that aids in the catalyst design by providing insights into physical and chemical structure. Physisorption experiments were performed using a Quantachrome Autosorb-iQ. The BET surface area was calculated using data in the $P/P_o$ range of 0.05-0.3, where a linear relationship for the BET isotherm is maintained.

XRD analysis was performed with a Philips X'pert XRD using a powder x-ray diffraction technique. The machine was operated in a Bragg angle (2θ) range of 15–80°. The step size was 0.06° and a dwell time of 1 s was used for each step. X'pert Highscore software was used to assist in data analysis.

TPR was performed using the Quantachrome Autosorb-iQ, mentioned above, using 50 mg of catalyst loaded into a quartz sample cell. Each sample was pretreated with helium while ramping the temperature 10° C./min from 25° C. to 110° C. and holding at temperature for 30 minutes. The sample was then cooled to 50° C. Following pretreatment, the carrier gas was switched to 5% $H_2/N_2$ and the temperature ramped to 1100° C. at 10° C./min. Gas analysis was performed using a thermal conductivity detector (TCD) measuring the conversion of $H_2$ under the temperature-programmed conditions.

A Hitachi S-800 SEM coupled to an Ametek EDAX was utilized to conduct SEM-EDS experiments. An excitation energy of 10 keV, a magnification of 1010, and a tilt angle of 30° were used in this analysis.

XPS measurements were taken with a Perkin-Elmer PHI 560 ESCA/SAM system under vacuum using an Mg filament. Binding energies were scanned in the 0-1030 eV range initially. A high resolution scan was performed on the Ni $2p_3$ peak in the binding energy range of 849-869 eV. RBG AugerScan 3 software was used for data analysis of the resulting spectrum.

Catalytic reactions were performed in a fixed-bed quartz u-tube reactor (ID=4 mm) at 1 atmosphere. Feed gas composition was controlled using Alicat Scientific mass flow controllers and adjusting the flow rates accordingly. Online analysis of the product gas was taken with a MKS Spectra (Cirrus) mass spectrometer (MS) connected in-line with the reactor. Before each experiment, the quartz reactor was loaded with 75.2 mg of catalyst into the bottom third of the quartz tube and supported on either side by inert quartz wool. The reaction vessel was positioned inside a Thermoscientific Thermolyne tube furnace. Reaction temperature was controlled by adjusting the furnace temperature program to the desired ramp rate or fixed temperature. Heat tape was used to heat reactant and product lines to prevent condensation from occurring prior to the catalyst bed and MS detector. Water was delivered to the reactant gas mixture through a heated water bubbler using helium as a carrier gas. All catalysts were first reduced with 10% $H_2$ in He while ramping the temperature from room temperature to 800° C. at 10° C./min and holding for 2 hours. After reducing the catalyst, bypass valves were used to stop flow through the reactor while the reforming gas mixture was adjusted to the desired composition. The valves were then reopened after the MS gave stable responses for each of the reactants. A gas hourly space velocity (GHSV) of 61000 $hr^{-1}$ was employed for all tri-reforming reactions, unless otherwise specifically stated. Conversion of $CH_4$ and $CO_2$ were calculated using the following formulae:

$CH_4$conv.=1−(mol $CH_4$ in product÷mol $CH_4$ in feed)   [Equation 11]

$CO_2$conv.=1−(mol $CO_2$ in product÷mol $CO_2$ in feed)   [Equation 12]

Immediately following each reaction, a temperature-programmed oxidation (TPO) was performed to quantify any coke present on the surface of the catalyst. After reactions, catalysts were quickly cooled to 115° C. under an inert (He) environment. The temperature was then ramped at 10° C./min to 700° C. and held for 1 hour as flow rates of $O_2$=2.5 SCCM and He=50 SCCM were used to oxidize the catalyst and convert surface coke to $CO_2$. Essentially all carbon was converted to $CO_2$ with insignificant amounts of other carbon-containing species produced. The product gas was analyzed by a MS detector and quantified by integrating the peak areas to determine the amount of carbon present as coke. TPO was used to measure the amount of coking and is reported in this study as average rate of coke formation per mass catalyst. This number is given as the mass of carbon deposited as coke/mass catalyst reaction time.

To understand how support composition, metal loading, and preparation influenced the surface area of the catalyst, BET analysis was performed and compared on multiple samples (Table 1). The pure oxide species had significantly lower surface areas than any of the mixed oxide supports, which suggests that the mixed oxide supports are not simply a mechanical mixture of the two species. Instead, a new oxide material with different physical properties from either of its pure components had been synthesized. This suggests a solid solution of Ce and Zr oxides formed using the co-precipitation technique. As more Ce is introduced into the structure of the catalyst, the surface area also increased. This effect reaches a maximum at a Ce:Zr ratio between 0.8:0.2 and 1:1 because the pure Ce oxide material has a dramatically lower surface area than the highest Ce content sample tested here (Ce:Zr=0.8:0.2). Upon loading of the Ni and Mg metals to the surface of each mixed oxide support material, the surface area decreased slightly. This is attributed to metal crystals forming within pores of the support and, in some cases, blocking the pathway.

TABLE 1

BET surface area for various supports and catalysts (8Ni8Mg refers to 8 % metal loading by wt. for each).

| Catalyst | BET Surface Area ($m^2/g$) |
|---|---|
| Pure Ceria Oxide | 28.3 |
| Pure Zirconia Oxide | 12.0 |
| $Ce_{0.16}Zr_{0.84}O_2$ | 30.5 |
| $Ce_{0.6}Zr_{0.4}O_2$ | 48.7 |
| $Ce_{0.8}Zr_{0.2}O_2$ | 50.1 |
| $Ce_{0.6}Zr_{0.4}O_2$-8Ni8Mg (wet impreg.) | 34.5 |
| $Ce_{0.6}Zr_{0.4}O_2$-8Ni8Mg (dep. precip.) | 43.3 |
| $Ce_{0.8}Zr_{0.2}O_2$-8Ni8Mg (wet impreg.) | 33.2 |
| $Ce_{0.8}Zr_{0.2}O_2$-8Ni8Mg (dep. precip.) | 44.1 |

Figure 2:
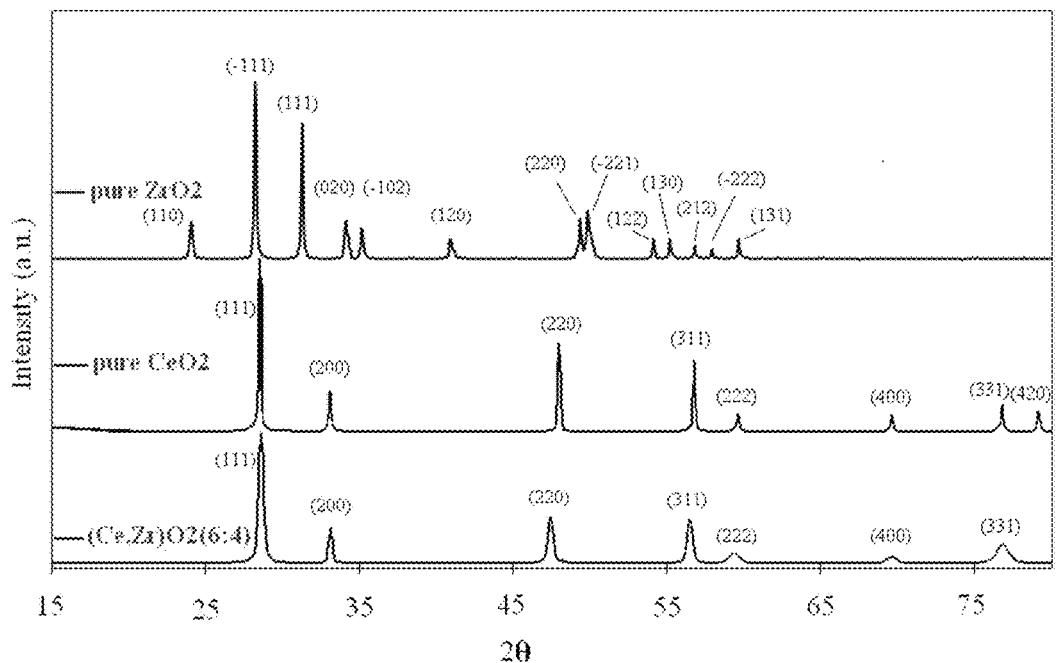
FIG. 2 is a graph that shows x-ray diffraction (XRD) profiles of example catalyst support materials.

Catalyst support materials were analyzed by XRD (FIG. 2) and compared to elucidate structural differences as the composition was altered. This figure compares the crystal structure of pure oxide species and the mixed oxide support with a Ce:Zr ratio of (0.6:0.4). Miller indices are also represented for each peak in FIG. 2.

Pure $ZrO_2$ is known to exist in the tetragonal and monoclinic phases. The XRD pattern of pure $ZrO_2$ obtained from this experimentation closely resembles characteristic peaks of the monoclinic phase. This is typical of $ZrO_2$ samples that have been calcined at higher temperatures. The XRD pattern from the pure $CeO_2$ shows characteristic peaks for a cubic fluorite structure. However, when these two pure oxide species were co-precipitated, no peaks could be identified that indicated a monoclinic $ZrO_2$ species and all peaks resembled the cubic fluorite structure found in pure $CeO_2$. This suggests that $ZrO_2$ is incorporated into the $CeO_2$ lattice and that a solid solution formed from the combination of these two oxide species. Peak broadening is seen in the mixed oxide sample compared to the pure oxides and is most likely due to lattice defects from the insertion of the smaller Zr cation into the $CeO_2$ lattice.

Figure 3:
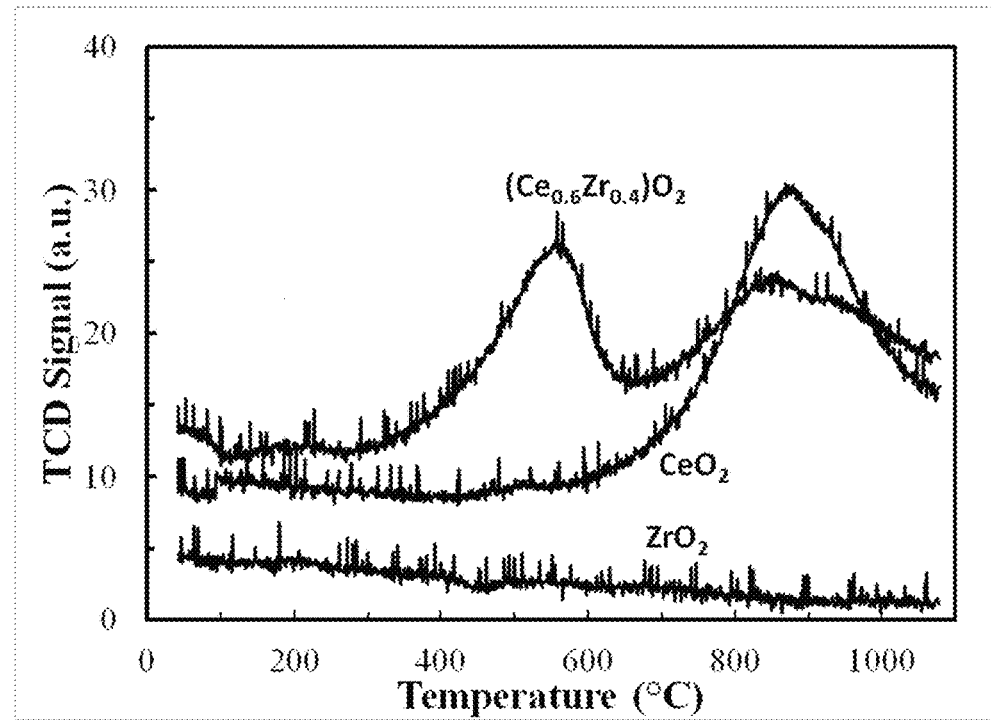
FIG. 3 is a graph that shows temperature-programmed reduction (TPR) profiles of catalyst support materials.

As shown in FIG. 3, different reduction peaks existed for the pure and mixed oxide supports. Both the pure $CeO_2$ and $ZrO_2$ show much higher temperatures needed to reduce these species compared to the mixed oxide. The pure $CeO_2$ support shows a maximum reduction peak around 865° C., while the pure zirconia support shows no reduction occurring at temperatures up to 1100° C. When these pure species were combined to form a mixed oxide support, a much lower reduction peak is seen to occur between 300-650° C. with a max adsorption peak at 555° C. This lower reduction temperature is attributed to a $(Ce, Zr)O_2$ solid solution forming with similar trends seen for other Ce:Zr ratios. The first and second reduction peaks in the mixed oxide are due to the surface and bulk reduction, respectively, and can be explained by the Binet et al. model for Ce reduction. Incorporation of Zr ions facilitates the valence change of Ce by enabling the volume change associated with the reduction of Ce. By incorporating Zr within support framework, oxygen mobility is increased, allowing oxygen migration between nearby cation channels. From the TPR experiments, it is seen that incorporating $ZrO_2$ into $CeO_2$ to form a mixed oxide improves oxygen storage capacity (OSC) and redox properties. $ZrO_2$ is also a more thermally stable compound that improves the mixed oxides' catalytic activity at the elevated temperatures used in reforming reactions.

Figure 4:
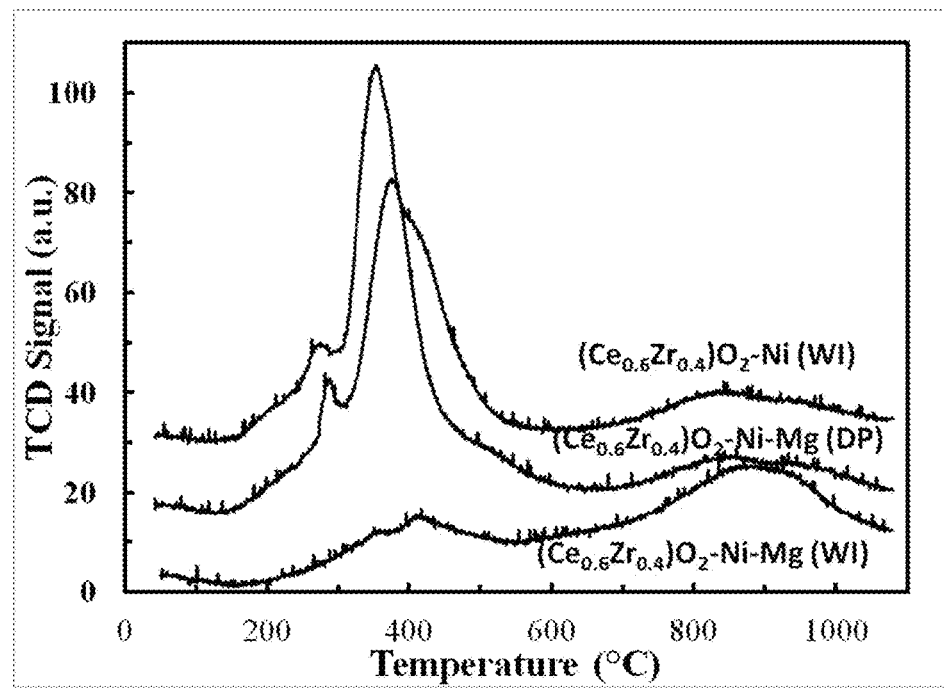
FIG. 4 is a graph that shows TPR profiles of $Ce_{0.6}Zr_{0.4}O_2$-8Ni (wetness impregnation), $Ce_{0.6}Zr_{0.4}O_2$-8Ni8Mg (deposition precipitation), and $Ce_{0.6}Zr_{0.4}O_{2-8}Ni8Mg$ (wetness impregnation).
Figure 5:
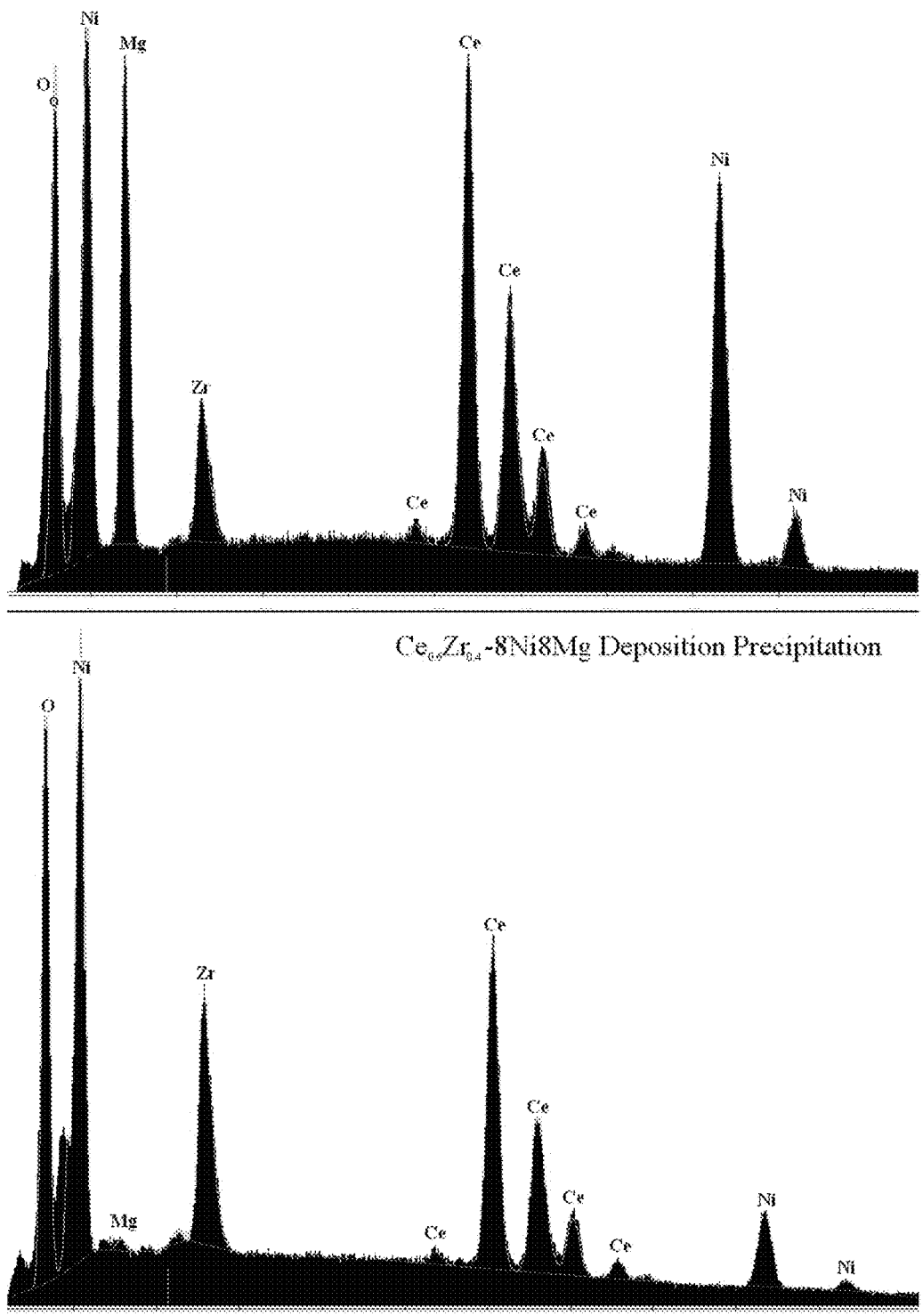
FIG. 5 includes graphs that show energy dispersive x-ray spectroscopy (EDS) results for $Ce_{0.6}Zr_{0.4}$-8Ni8Mg loaded by wetness impregnation and deposition precipitation.

TPR was also utilized to gain a better understanding of how the Ni interactions between Mg and the support are affected when using different metal loading techniques. The TPR profiles (FIG. 4) of catalysts loaded with Ni and Mg using WI and DP methods are compared to a catalyst with only Ni loaded via WI. Interestingly, when Ni and Mg were loaded by DP, the reduction profile closely resembled that of the catalyst with only Ni loaded onto the surface. When Ni and Mg were loaded by WI, most of the reduction occurred at higher temperatures. The lower temperature reduction peaks seen are associated with isolated Ni and weakly interacting Ni with the support and Mg. The higher temperature reduction seen in the WI catalyst is indicative of a strong interaction occurring between Ni and Mg. This result was found as a surprise since DP is usually associated with higher dispersion of smaller particles and thus stronger interactions. The lower reduction peak in the DP-prepared catalyst could be attributed to higher dispersion causing fewer interactions between the Ni and Mg. However, upon further experimentation using SEM coupled with EDS (FIG. 5), it was determined that less Mg had been loaded onto the DP-prepared catalysts compared to the WI-prepared catalyst and explains why the reduction peak of the DP catalyst resembled the catalyst with only Ni loaded onto the surface by WI. The high temperature reduction peak in the WI catalyst containing Ni and Mg species is thus attributed to more interfaces between Ni and Mg with stronger interactions between them.

XPS was utilized to measure the binding energies of various components present in the reduced catalysts prepared by WI with the support makeup of $Ce_{0.4}Zr_{0.6}O_2$. An initial broad range scan was performed to identify the major species present and the binding energies associated with these species.

Figure 6:
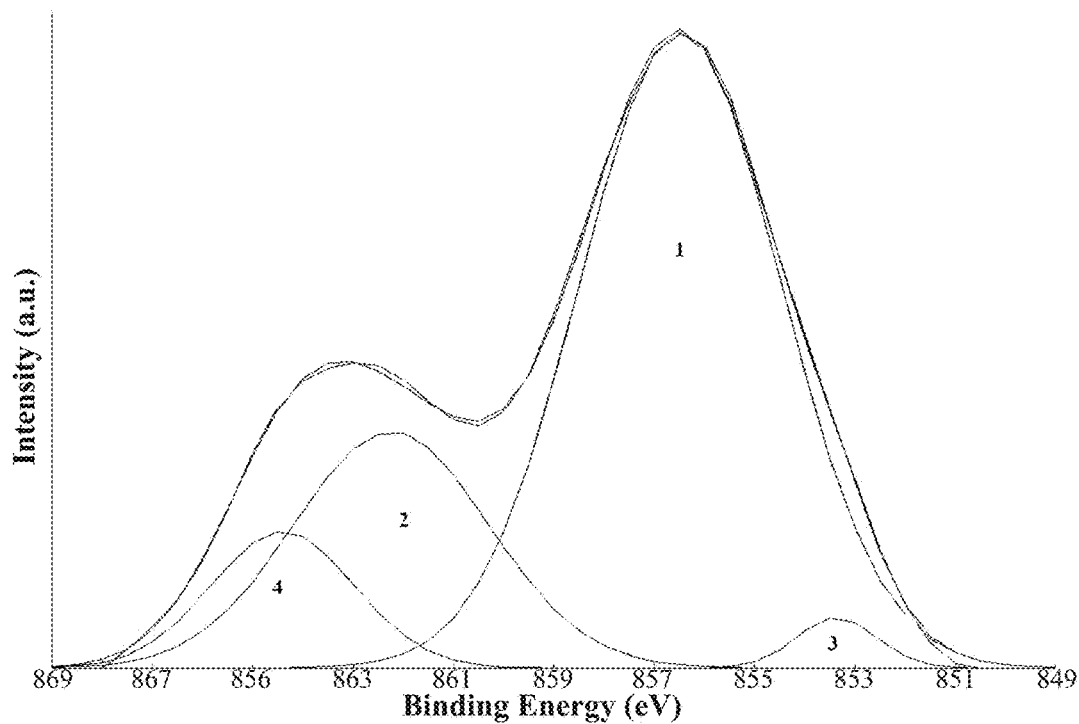
FIG. 6 is a graph that shows the surface spectrum by x-ray photoelectron spectroscopy (XPS) of the $Ni2p_{3/2}$ peak for reduced $Ce_{0.6}Zr_{0.4}$-8Ni8Mg loaded by wetness impregnation.

A high resolution scan of the Ni $2p_{3/2}$ peak centered at a binding energy near 856 eV was then performed to identify the interactions between the Ni, mixed oxide support, and MgO of the catalyst loaded with 8 wt % Ni and Mg. A curve-fit summary was produced from this scan, the results of which can be found in FIG. 6 where the majority of Ni is oxidized. The major peak (856 eV) is associated with oxidized Ni and could be associated with interactions to the mixed oxide support, MgO, or hydroxyl groups. The second (near 862 eV) and third largest (near 865 eV) peaks are attributed to a satellite peak of the main peak. The small peak near 853 eV is the only signature of metallic Ni. These results indicated strong interactions with the Mg and the mixed oxide support, but only limited conclusions can be made because of the complex spectrum of Ni and possible oxidation at the surface.

Figure 7:
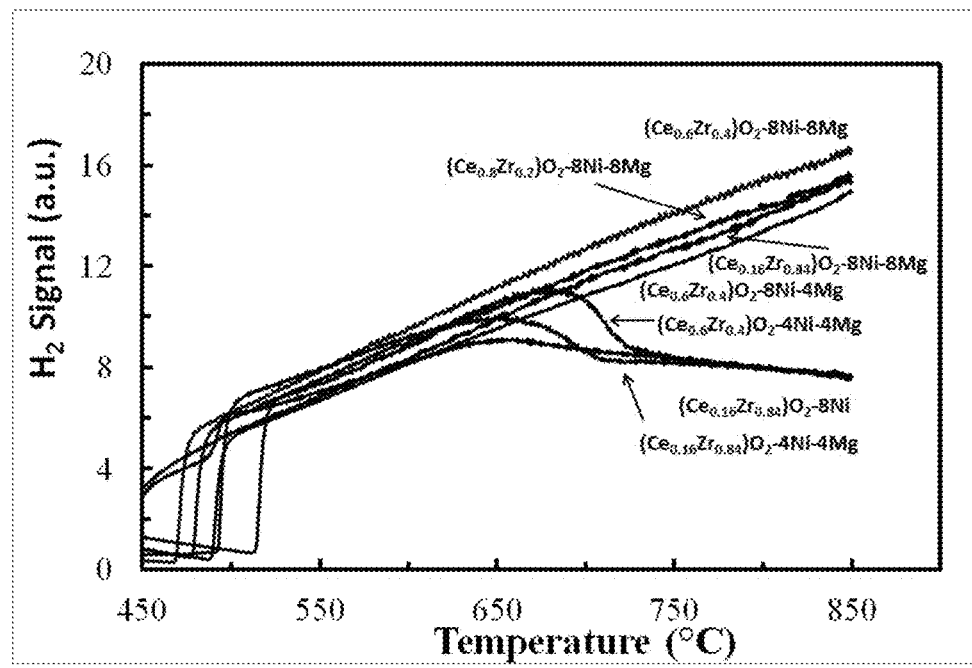
FIG. 7 is a graph that shows $H_2$ production for initial catalytic testing using steadily ramped temperature at 10° C./min with a gas composition of $(CH_4:CO^2:O_2:H_2)=(1:1:0.1:0.1)$.

Various catalyst formulations were tested to study the consequences of altering the support mixture and the ratios/amounts of metals loaded onto the catalyst. These catalysts were each tested under the same conditions while steadily ramping the temperature. All catalysts were prepared using the same WI preparation technique. Results were compared and are shown in FIG. 7, which illustrates the $H_2$ production from various catalysts tested while steadily ramping the temperature at 10° C./min. $H_2$ production is only shown in FIG. 7 for ease of interpretation, but $CO_2$ and $CH_4$ conversions were also analyzed. The effects of varying the support makeup ratio were compared by holding the metal weight percentage and ratios constant. The lower Ce:Zr ratios of 0.16:0.84 in the support led to lower $H_2$ production, $CH_4$ conversion, and $CO_2$ conversion. When Ce:Zr ratios were increased to 0.8:0.2, the $H_2$ production, $CH_4$ conversion, and $CO_2$ conversion slightly increased. Adjusting Ce:Zr ratios to a more even ratio of 0.6:0.4 gave the best results with the highest $H_2$ production, $CH_4$ conversion, and $CO_2$ conversions. This finding is in agreement with the charge channeling effect created by nearby cations. By incorporating a more even ratio of Ce:Zr, oxygen mobility and redox properties are improved, allowing transport of oxygen to appropriate sites and preventing coking on the Ni metal surface. Thermal stability was seen in all mixed oxide support ratios and is attributed to $ZrO_2$ high thermal stability.

The impacts of metal loading ratios and weight percentage on the catalyst were explored by holding the support ratio constant and varying the metal loading quantities. Different Ni amounts (4% and 8%) were loaded onto the same support composition. In all cases, the lower weight percentage of Ni lead to a plateau effect and a low $H_2$ production was seen. The plateauing effect describes the tendency of the production of a certain compound, in this case $H_2$, to remain unchanged even when temperature is increased. When 8% Ni was loaded onto the catalyst, the plateauing effect on $H_2$ production at higher temperatures is no longer seen. The amounts and ratios of Mg were also varied to study its effect on catalyst performance. Again, catalysts with the same support composition and metal-loading technique were compared while varying the metals loaded onto the surface. The catalyst with no Mg loaded, suggesting coking on this sample onto the surface, had the slowest rates of $H_2$ production and quickly plateaued even when higher Ni amounts were loaded onto the surface. At a Ni:Mg weight percentage ratio of 2:1, $H_2$ production rates were increased and no plateauing of the $H_2$ production was seen with a steady rise in production as temperatures were increased. Higher amounts of $H_2$ and the fastest rate of $H_2$ production were seen when Ni:Mg weight percentage ratios of 1:1 were loaded onto the catalyst surface. This effect can be explained by the facilitation of the redox mechanism involved in methane reforming with increased interface between Ni and Mg. Metal weight percentage ratios approaching unity gave more interfaces between Ni and Mg. This facilitates $CO_2$ adsorption/dissociation and oxygen movement to the reduced Ni surface where it could react with the adsorbed carbon from $CH_4$. Basic promoters like MgO have an affinity for $CO_2$ due to its acidic nature. This is an added advantage in $CO_2$ reforming because $CO_2$ is normally a very stable molecule and a catalytic reaction is needed for quick dissociation.

Reactions were studied under controlled temperature programs with the optimum temperature range found between 750-850° C. At the lower end of this range, higher $H_2$:CO ratios were produced due to the steam reforming and water-gas shift (WGS) reactions (Equations 2 and 3) being more favorable at these temperatures. However, lower $CO_2$ conversions were obtained at the lower temperatures. Because $CO_2$ reforming is favorable at high temperatures, it was determined that $CO_2$ conversion increased with increasing temperature in this range. At 800° C., $CO_2$ conversions remained high and desired $H_2$:CO ratios could be achieved without catalyst deactivation. At this temperature, coke gasification reactions can occur while maintaining high levels of steam reforming and POM to produce desired $H_2$:CO ratios. At higher temperatures, $CO_2$ conversion increases but $H_2$:CO ratios dropped not only due to the increase in CO production, but also to less $H_2$ production. This result occurs because $H_2$ production decreases as $CO_2$ reforming dominates the reaction making steam reforming and POM reactions less favorable at higher temperatures.

Gas composition greatly affects the reaction products. In tri-reforming, many reactions are occurring at one time and finding the correct ratios of reactants is not trivial. During tri-reforming reactions, it was found that conversion of $O_2$ was the highest of all oxidants, the $O_2$ completely being consumed. Oxygen seems to have a high affinity for active sites on the catalyst and tends to react quickly. Remaining active sites or those where $O_2$ had already disassociated are available for the other reactants. $H_2O$ and $CO_2$ compete for the same active sites. Therefore, experiments were performed to understand how altering these two reactant concentrations influenced product ratios. Table 2 helps explain these effects and shows that increasing the $H_2O$ ratio in the feed will increase the $H_2$:CO ratio. However, there is a point at which higher $H_2O$ ratios led to a decrease in $CO_2$ conversion. One of the goals in tri-reforming is to maintain high $CO_2$ conversions while still producing desired $H_2$:CO ratios. High $CO_2$ conversion made the process more environmentally friendly and improved efficiency in FTS for liquid hydrocarbons. The results in Table 2 suggest that the adsorption of $H_2O$ blocks the $CO_2$ adsorption sites leading to higher $H_2$:CO ratios and inhibition of $CO_2$ reforming. Lower than expected $H_2O$ concentrations in the feed gas were found to produce high concentrations of $H_2$ without greatly sacrificing $CO_2$ conversion. From Table 2, a $CH_4$:$CO_2$:$H_2O$:$O_2$ ratio of 1:0.7:0.23:0.2 produced desired $H_2$:CO ratios above 2. This result demonstrates the optimum syngas composition for FTS applications can be achieved while maintaining high $CO_2$ conversions at lower $H_2O$ ratios. At these conditions, the catalyst still showed a high resistance to coke formation on the catalyst surface.

TABLE 2

Comparison of reaction results at T = 800° C. with $Ce_{0.6}Zr_{0.4}O_2$-8Ni8Mg (wet impreg.) for a variety of gas feed ratios.

| Gas Composition ($CH_4$:$CO_2$:$H_2O$:$O_2$) | Rxn Time | $H_2$:CO | $CH_4$ Conv. (%) | $CO_2$ Conv (%) | Coke ($g_{coke}/g_{cat}$-hr) |
|---|---|---|---|---|---|
| (1:1:0:0.1) | 30 min | 1.1 | 74.7 | 71.1 | — |
|  | 4 hr | 0.9 | 60.9 | 59.8 | 2.0E−02 |
| (1:0.7:0:0.2) | 30 min | 1.8 | 99.1 | 87.4 | — |
|  | 4 hr | 1.7 | 99.1 | 88.0 | 2.4E−03 |

TABLE 2-continued

Comparison of reaction results at T = 800° C. with $Ce_{0.6}Zr_{0.4}O_2$-8Ni8Mg (wet impreg.) for a variety of gas feed ratios.

| Gas Composition ($CH_4$:$CO_2$:$H_2O$:$O_2$) | Rxn Time | $H_2$:CO | $CH_4$ Conv. (%) | $CO_2$ Conv (%) | Coke ($g_{coke}/g_{cat}$-hr) |
|---|---|---|---|---|---|
| (1:0.7:0.85:0.2) | 30 min | 2.1 | 98.9 | 86.9 | — |
|  | 4 hr | 2.0 | 98.9 | 87.8 | 6.2E−04 |
| (1:0.7:23:0.2) | 30 min | 2.2 | 98.8 | 76.3 | — |
|  | 4 hr | 2.1 | 97.3 | 77.6 | 5.1E−04 |
| (1:0.7:0.3:0.2) | 30 min | 2.3 | 99.5 | 69.0 | — |
|  | 4 hr | 2.1 | 99.4 | 70.2 | 3.6E−04 |
| (1:0.7:0.5:0.2) | 30 min | 2.3 | 99.6 | 66.3 | — |
|  | 4 hr | 2.2 | 99.6 | 65.6 | 3.7E−04 |

An added benefit of the current results for FTS are the low steam amounts because steam is reported to deactivate catalysts. At the reaction temperature of 800° C. and the composition ratios mentioned above, tri-reforming over $Ce_{0.6}Zr_{0.4}$-8Ni8Mg produced an upgraded syngas with desired $H_2$:CO ratios for FT applications that achieved $CO_2$ conversions above 76% and maintained resistance to coke formation at lower steam ratios. Negligible levels of coke were detected in TPO experiments and catalyst activity remained high at the above-reaction conditions. The ability to maintain high levels of $CO_2$ conversion without deactivation becomes a highly attractive option since $CO_2$ in FT feedstock syngas increases the $H_2$ demand and $H_2$:CO ratios higher than 2 will be needed to produce low concentrations of olefins and oxygenates in the FT synthesized product.

In an effort to determine the effect of the GHSV on the product composition and insight into which reactions are occurring, the amount of catalyst was increased. The increase in catalyst amount forced reactant gas residence times to be longer (Table 3). The amount of catalyst used in the experiments ranged from 2.5-2.9 times (186-218 mg) the amount used in previous studies (i.e., 75 mg). A feed gas $CH_4$:$CO_2$:$H_2O$:$O_2$ ratio of 1:0.7:0.5:0.2 was fed to the reactor. GHSV was calculated to be approximately 21000 hr$^{-1}$ and 25000 hr$^{-1}$ when 218 mg and 186 mg catalyst, respectively, were used to perform the reaction. Whereas $CH_4$ conversions remained relatively unchanged, $CO_2$ conversions were slightly lower and $H_2$:CO ratios were significantly reduced compared to the previous studies in which the GHSV-61000 hr$^{-1}$. It is proposed that as the feed gas initially reacts and creates higher $H_2$ concentration, the reverse WGS reaction becomes more favorable further down the catalyst bed. This could be an indication of steam reforming reactions (Eqs. 2 and 3) approaching equilibrium. This suggests that there may be an advantage to using higher GHSV to maintain higher $H_2$ production.

TABLE 3

GHSV comparison at T = 800° C. with $Ce_{0.6}Zr_{0.4}O_2$-8Ni8Mg (wet impreg.) for a gas feed ratio of $CH_4$:$CO_2$:$H_2O$:$O_2$ = 1:0.7:0.5:0.2.

| GHSV (hr$^{-1}$) | Rxn Time | $H_2$:CO | $CH_4$ Conv. (%) | $CO_2$ Conv. (%) |
|---|---|---|---|---|
| 61000 | 5 min | 2.3 | 99.6 | 66.3 |
|  | 4 hr | 2.2 | 99.6 | 65.6 |
| 25000 | 5 min | 1.6 | 99.4 | 63.3 |
|  | 4 hr | 1.6 | 99.5 | 62.7 |
| 21000 | 5 min | 1.7 | 98.3 | 57.2 |
|  | 4 hr | 1.6 | 98.3 | 54.7 |

By decreasing residence time, the ability to limit reactions that consume $H_2$ may be possible. However, even at the lower GHSV conditions, $H_2$:CO ratios were maintained between 1.55-1.66. Therefore, if $H_2$ supplementation is needed for FT processing of the tri-reformed gas, the amount of $H_2$ needed to be added to the tri-reforming process will be significantly lower than compared to more traditional reforming processes. These other reforming processes will also be significantly more expensive as higher amounts of steam will be needed and/or coking reactions will limit catalyst lifetime.

Figure 8:
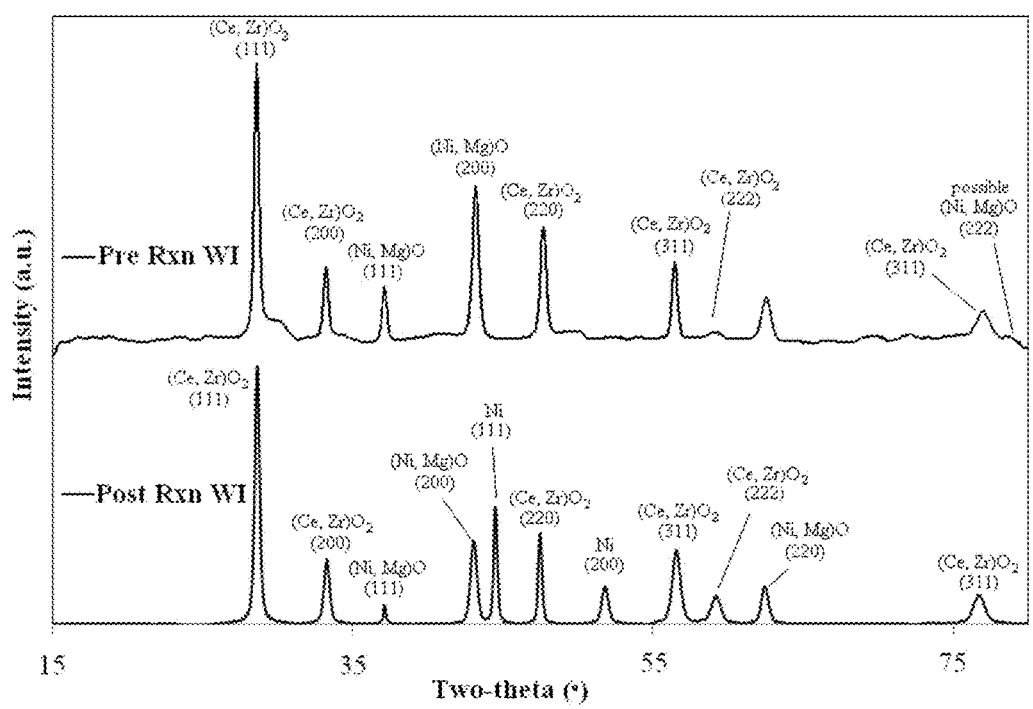
FIG. 8 is a graph that shows XRD profiles of $Ce_{0.6}Zr_{0.4}$-8Ni8Mg loaded by wetness impregnation before and after tri-reforming.

Post-reaction characterizations were performed on the $Ce_{0.6}Zr_{0.4}$-8Ni8Mg loaded by WI. After 4 hours of reaction at 800° C. and a feed gas $CH_4$:$CO_2$:$H_2O$:$O_2$ ratio of 1:0.7: 0.5:0.2, the catalyst surface area decreased from 34.5 to 22.1 $m^2$/g. This change is attributed to using a higher reaction temperature than the final calcining temperature used to synthesize the catalyst. Comparing initial and final conversions, catalyst performance appeared to be minimally influenced by the change in surface area (Tables 2 and 3). The formation of coke did not appear to play a role in the change in catalyst surface area. This finding is supported by the negligible amounts of coke detected using post-reaction TPO experiments. No evidence of crystalline carbon is present in the XRD pattern of the post-reaction sample (FIG. 8).

The post-reaction sample shows Ni in the reduced form, which is expected due to the high production of $H_2$ during the reforming reaction. Peaks characteristic of reduced Ni show higher intensity while the characteristic peaks for (Ni,Mg)O decreased in the post-reaction sample, indicating that Ni species in the (Ni, Mg)O solid solution are reducible under reaction conditions for those catalysts prepared by WI. This was an excellent result because the deactivation of Ni-reforming catalysts has been attributed to the inability to reduce Ni from an inactive oxide phase to a reduced Ni phase. Post-reaction samples showed the same (Ce, Zr)$O_2$ pattern as the pre-reaction sample, indicating that the cubic fluorite phase is stable under the reaction conditions employed.

In view of the above discussion, the catalyst used in the tri-reformer 18 of FIG. 1 comprises a mixture of nickel (Ni), magnesium (Mg), cerium (Ce), and zirconium (Zr). In some embodiments, the catalyst comprises $Ce_{(x)}Zr_{(1-x)}$-yNizMg. In such a case, x is the molar amount of Ce and (1−x) is the molar amount of Zr in the support, while y and z indicate the mass loading of Ni and Mg, respectively. In some embodiments, x, y, and z are integers and x and y are less than one. As indicated above, in one example, x=0.6, y=8, and z=8, in which case the catalyst is $Ce_{0.6}Zr_{0.4}$-8Ni8Mg.

With further reference to FIG. 1, the tri-reformer 18 alters the ratios of the various components of the LFG to one in which FTS can be performed to produce liquid fuel. More particularly, the tri-reformer 18 produces synthesis gas that has a $H_2$ to CO ratio of approximately 2:1, meaning that the synthesis gas contains twice as much $H_2$ than CO. In addition to $H_2$ and CO, the synthesis gas may contain $CO_2$ and water vapor. In some embodiments, the tri-reformer 18 is configured as a packed-bed reactor and the LFG is flowed through the catalyst at an elevated temperature in the range of approximately 600 to 800° C. Although that temperature can be maintained by further combustion of the LFG, additional energy can be input into the tri-reformer 18, as indicated in FIG. 1, to ensure the desired temperature is maintained. As is also shown in FIG. 1, water can be provided to the tri-reformer 18 to assist in the reaction.

As noted above, the output from the tri-reformer 18 is synthesis gas having a $H_2$:CO ratio of approximately 2:1. Because the temperature of that synthesis gas is higher than is needed for FTS, the gas can be cooled using a syngas heat recovery unit 20, which lowers the temperature of the gas to approximately 200° C. to 220° C. In some embodiments, the heat recovery unit 20 can comprise a heat exchanger and the extracted heat energy can be used for other purposes, such as heating the tri-reformer 18.

Once the synthesis gas is at the desired temperature, it is provided to the second reactor of the system 10, the FTS reformer 22. The FTS reformer comprises a further catalyst that converts the synthesis gas into liquid fuel. In some embodiments, the catalyst is a cobalt-silica catalyst. In testing, silica supported cobalt eggshell was used as the active catalyst material for the production of liquid hydrocarbon from the resultant syngas. The choice of this eggshell catalyst was based on the desire to increase the selectivity towards middle distillate products. Silica gel support was selected mainly due to its inertness, high surface area, and versatile nature (hydrophobic/hydrophilic).

The catalyst, along with conductive inert particles, was placed in a fixed bed reactor for the conversion of syngas. The bench scale reactor comprised a cylindrical tube having 0.75 inch OD (1.905 cm) and 17 inch (43.18 cm) length. The Co/$SiO_2$ eggshell catalyst was first reduced in pure hydrogen at 673 K (400° C.). After reduction for 16 hours, the reactor temperature was reduced to 453 K (180° C.) and syngas mixed with hydrogen (to get the appropriate 2:1 ratio of $H_2$ to CO) was delivered to the fixed bed reactor at a rate of 0.7 N L/min. The choice of flow rate was based on recommended values of space velocity in which the favorable range (for CO conversion) is from 2-10 L/g/h. The space velocity in this process was 2.0 L/g(reactor contents)/hr. Maximum conversions have been earlier reported at this space velocity. After adjusting the flow rate, temperature was gradually raised to 473K (200° C.) to carry out the Fischer Tropsch reaction (Pressure=2 MPa). The temperature was then raised to 493K (220° C.). Based on the fact that a temperature of 493 K (220° C.) will result in heavier chain growth for an eggshell catalyst and less methane, the operation was continued at this temperature.

Precise control of the catalyst bed temperature during the startup (pore filling time) of FTS is essential to avoid thermal runaway. To overcome this limitation, inert materials, such as silicon carbide, having high thermal conductivity were added to the fixed bed. Active catalyst and SiC were effectively mixed at a ratio of 1:3 within the reactor.

Table 4 summarizes results at the end of five-day operation of the fixed bed reactor with biomass derived syngas. As expected, the eggshell morphology resulted in high selectivity of middle distillates. In previous work by the inventors on pure gases, it was identified that a temperature of 483 K (210° C.), results in significant production of lighter hydrocarbons. The current operation at 487 K (214° C.) reduced the fraction of lighter hydrocarbons ($C_{1-4}$) produced when compared with the earlier work. The formation of $CO_2$ is still high, however some of the previous research work on biomass has reported this number even at lower conversions with minimal $CO_2$ in the feed. The CO conversion was lower than pure surrogates reported earlier, due to the presence of inert component ($CO_2$/$N_2$/hydrocarbons). The kinetic equations provided by other researchers suggest that the rate is dependent on temperature and partial pressure of $H_2$ and CO. For a same total pressure, the partial pressure of reactive components decreases in the presence of inert components. However, higher conversion (75 vs. 60%) has been considered in modeling because of the effective removal of inert $CO_2$ and the absence of $N_2$.

TABLE 4

Eggshell Catalyst performance with biomass derived syngas under FTS conditions i.e. 503 K and 2.0 MPa

| Catalyst | CO conv. (%) | Productivity[a] (lit/day) | Selectivity (Mol %) | | | STY[b] g/(g-cat.h) | Wt % in Liquid HC | | |
|---|---|---|---|---|---|---|---|---|---|
| | | | H-C$_{light}$ | CO$_2$ | C$_5^+$ | | C$_{5-12}$ | C$_{13-25}$ | C$_{25}^+$ |
| Cp/Sio2 | 60 | 0.15 | 18.7 | 6.3 | 74.4 | 1.6 | 28.38 | 63.09 | 6.53 | a) Productivity of liquid fuel in a day
b) Space time yield of hydrocarbon with carbon number greater than 5

Figure 9:
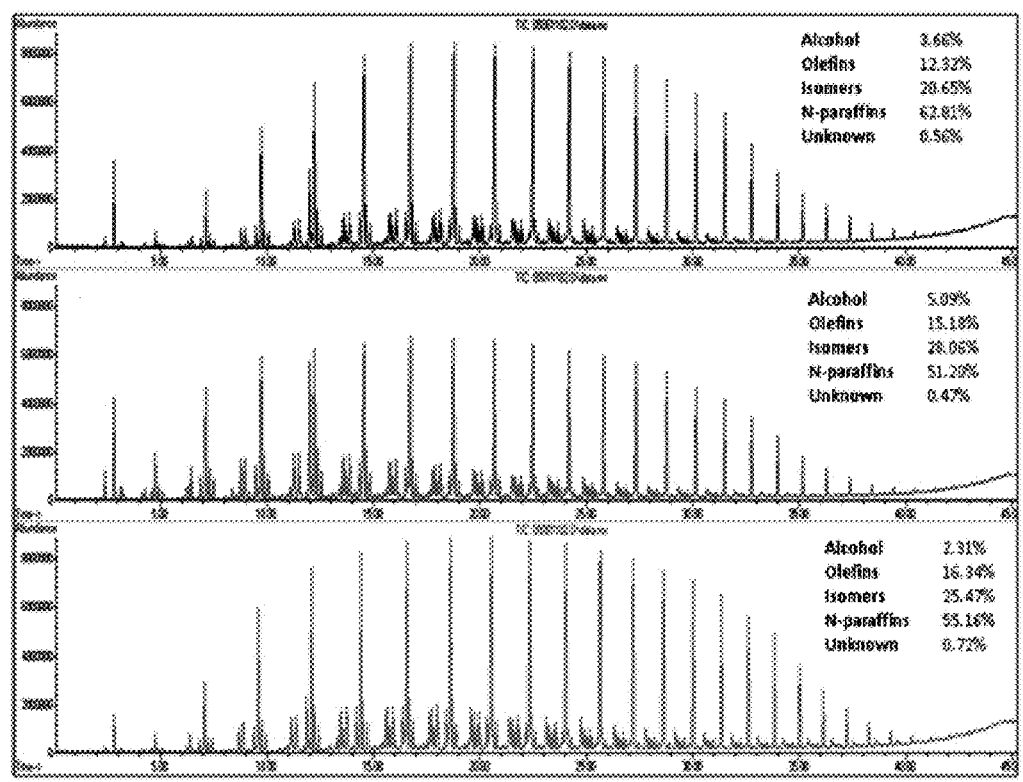
FIG. 9 is a gas chromatography distribution of liquid hydrocarbons using the HP-5 column.
Figure 10:
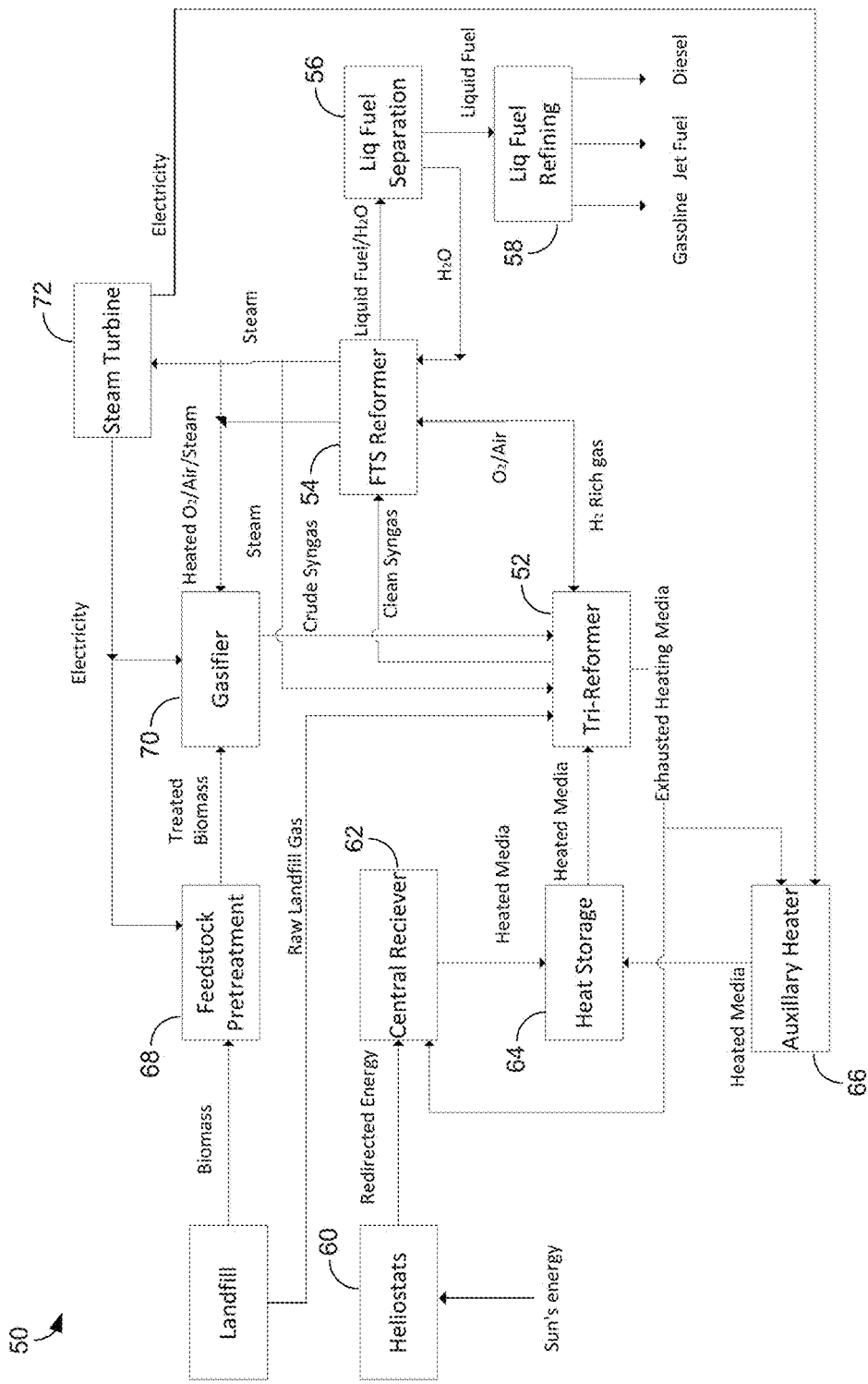
FIG. 10 is a block diagram of a second embodiment of a liquid fuel production system.

Due to the optimization of eggshell design and tight control of reaction parameters, the C$_5$+ selectivity was high, as shown in Table 4. FIG. 9 represents GC distribution of liquid hydrocarbons using HP-5 column. Analysis by mass spectrometer (Agilent 5975C) showed the presence of alcohols and olefins in addition to the expected paraffinic hydrocarbons. Hence, oxygenates are effectively produced in the FTS process with a cobalt catalyst. The presence of isomers is also visible between the bands of paraffin. These isomers enhance the octane/cetane value of the fuel. As shown in FIG. 9, the cobalt catalyst showed excellent reproducibility over the duration of test run.

With reference back again to FIG. 1, it is noted that the use of only two reactors (i.e., the tri-reformer 18 and the FTS reformer 22) is unique because existing technologies typically require three separate reactors, including a WGS reactor. In the system 10, however, there is no WGS shift reactor. Therefore, the system 10 simplifies the process and is less costly to construct. The ability to use two reactors instead of three in large part is the result of the conditions within the tri-reformer 18 and the nature of the catalyst, which is specifically suited for a mixture of methane and carbon dioxide found in the LFG. The unique combination of the conditions and catalyst used in the reactor enable the production of synthesis gas in the desired hydrogen to carbon monoxide ratio.

The liquid fuel produced by the FTS reformer 22 is delivered to a liquid fuel heat recovery unit 24 in which the fuel is cooled. In some embodiments, the heat recovery unit 24 can also comprise a heat exchanger to achieve this cooling.

The liquid fuel produced by the FTS reformer 22 may contain different types of fuels, such as diesel fuel and jet fuel. In such a case, the fuels can be separated using a liquid fuel separation unit 26. As is shown in FIG. 1, outputs from the separation unit 26 can include water, which can be delivered to the tri-reformer 18 as steam, and fuel gas (e.g., CH$_4$) that can be provided to the flare unit 16 and a fuel combustion unit 28, which can be used to provide heat energy to the tri-reformer. If further types of fuel, such as gasoline, are desired, a liquid fuel refining unit 30 can be used to produce that other fuel. For example, if gasoline is desired, the diesel fuel can be cracked to produce the gasoline.

FIG. 9 illustrates a second embodiment of a fuel production system 50. The system 50 is similar in many ways to the system 10 described in relation to FIG. 1, but utilizes solar energy to convert LFG into liquid fuel. Like the system 10, the system 50 includes a tri-reformer 52 that produces synthesis gas having a hydrogen H$_2$:CO ratio of approximately 2:1, an FTS reformer 54 that converts the synthesis gas into liquid fuel, and no further reactor, such as a WGS reactor. The liquid fuel provided by the system 50 can be separated by a liquid fuel separation unit 56 and refined by a liquid fuel refining unit 58. As is further shown in FIG. 9, H$_2$-rich gas from the FTS reformer 54 can be provided back to the tri-reformer 52, as can steam and crude synthesis gas from other sources described below. In addition to the synthesis gas from the tri-reformer 52, O$_2$ and/or air can be input into the FTS reformer 54, as can water from the liquid fuel separation unit 56.

Instead of using combustion to provide the heat needed for the reaction in the tri-reformer 52, the system 50 utilizes solar energy generated using a solar collector. In the illustrated embodiment, the solar collector includes heliostats 60 that focus the sun's energy on heating media within a central receiver 62. The heated media can then be stored in a heat storage unit 64 and, when needed, can be provided to the tri-reformer 52. Optionally, an auxiliary heater 66 can be used to heat the media within the storage unit 64. In such a case, the heater 66 can be driven with the exhausted heating media from the tri-reformer 52 and/or electricity from a source described below.

In some embodiments, the system 50 can also generate liquid fuel from biomass from the landfill. In such a case, the biomass can be input into a feedstock pretreatment unit 68 that pretreats the biomass by, for example, drying it and removing components that cannot be used in the fuel generation process (e.g., metal, glass, etc.). The treated biomass can be provided to a gasifier 70 that extracts crude synthesis gas from the biomass. This is accomplished by adding heated O$_2$, air, and steam to the gasifier 70 and heating the mixture. The energy needed to heat the mixture can, for example, be provided by a steam turbine 72 that operates using steam output from the FTS reformer 54. The electricity produced by the turbine 72 can also be provided to the auxiliary heater 66 described above. The heated O$_2$, air, and steam can be provided to the gasifier 70 from the FTS reformer 54. The crude synthesis gas that is output from the gasifier 70 can then be provided to the tri-reformer 52.

Claimed are:

1. A method for producing liquid fuel from landfill gas, the method comprising:
   providing landfill gas to a tri-reformer;
   performing a tri-reforming process on the landfill gas within the tri-reformer to convert the landfill gas into synthesis gas, wherein the tri-reforming process combines carbon dioxide reforming, steam reforming, water-gas shifting, and methane oxidation and wherein the synthesis gas has a H$_2$:CO ratio of approximately 2:1;
   providing the synthesis gas to a Fischer-Tropsch synthesis (FTS) reformer; and
   converting the synthesis gas into liquid fuel within the FTS reformer.

2. The method of claim 1, wherein the tri-reformer contains a first catalyst and the FTS reformer contains a second catalyst.

3. The method of claim 2, wherein the first catalyst comprises one or more of nickel, magnesium, cerium, and zirconium.

4. The method of claim 2, wherein the first catalyst comprises $Ce_{(x)}Zr_{(1-x)}$-yNizMg and x, y, and z are integers.

5. The method of claim 2, wherein the first catalyst comprises $Ce_{0.6}Zr_{0.4}$-8Ni8Mg.

6. The method of claim 2, wherein the second catalyst is a cobalt-silica catalyst.

7. The method of claim 1, further comprising providing heat to the tri-reformer generated using solar energy.

8. The method of claim 7, wherein providing heat generated using solar energy comprises providing heat generated by a solar collector that focuses the sun's energy on a heating medium within a central receiver.

9. The method of claim 1, wherein no reactors other than the tri-reformer and the FTS reformer are used to convert the landfill gas into liquid fuel.

10. The method of claim 1, further comprising cleaning the landfill gas with a cleaning unit prior to providing the landfill gas to the tri-reformer.

11. The method of claim 10, further comprising delivering some of the landfill gas from the cleaning unit to a combustion unit that provides heat to the tri-reformer.

12. The method of claim 1, further comprising cooling the synthesis gas from the tri-reformer in a heat recovery unit prior to providing the synthesis gas to the FTS reformer.

13. The method of claim 1, further comprising removing heat from the FTS reformer using a heat recovery unit.

14. The method of claim 1, further comprising refining the liquid fuel from the FTS reformer.

15. The method of claim 1, further comprising delivering some of the gas from the FTS reformer to a combustion unit that provides heat to the tri-reformer.

* * * * *